United States Patent
Sohn et al.

(10) Patent No.: US 12,246,083 B2
(45) Date of Patent: Mar. 11, 2025

(54) SUNSCREEN COMPOSITIONS COMPRISING BUTYL METHOXYDIBENZOYLMETHANE, TRIAZINE DERIVATIVES AND PHOTOSTABILIZER

(71) Applicant: BASF SE, Ludwigshafen am Rhein (DE)

(72) Inventors: Myriam Sohn, Grenzach-Wyhlen (DE); Stanislaw Krus, Grenzach-Wyhlen (DE); Marcel Schnyder, Grenzach-Wyhlen (DE); Stephanie Acker, Grenzach-Wyhlen (DE)

(73) Assignee: BASF SE, Ludwigshafen am Rhein (DE)

( * ) Notice: Subject to any disclaimer, the term of this patent is extended or adjusted under 35 U.S.C. 154(b) by 721 days.

(21) Appl. No.: 17/439,657

(22) PCT Filed: Mar. 13, 2020

(86) PCT No.: PCT/EP2020/056926
§ 371 (c)(1),
(2) Date: Sep. 15, 2021

(87) PCT Pub. No.: WO2020/187773
PCT Pub. Date: Sep. 24, 2020

(65) Prior Publication Data
US 2022/0151899 A1 May 19, 2022

(30) Foreign Application Priority Data
Mar. 15, 2019 (EP) .................... 19163171

(51) Int. Cl.
*A61K 8/49* (2006.01)
*A61K 8/35* (2006.01)
*A61Q 17/04* (2006.01)

(52) U.S. Cl.
CPC .............. *A61K 8/4966* (2013.01); *A61K 8/35* (2013.01); *A61Q 17/04* (2013.01); *A61K 2800/30* (2013.01); *A61K 2800/52* (2013.01)

(58) Field of Classification Search
CPC .... A61K 8/4966; A61K 8/35; A61K 2800/30; A61K 2800/52; A61K 8/37; A61K 8/40; A61K 8/85; A61Q 17/04
See application file for complete search history.

(56) References Cited

U.S. PATENT DOCUMENTS

| | | | |
|---|---|---|---|
| 6,419,908 B1 † | 7/2002 | Candau | |
| 7,357,919 B2 † | 4/2008 | Candau | |
| 7,368,105 B2 † | 5/2008 | Candau | |
| 7,431,917 B2 † | 10/2008 | Candau | |
| 8,303,940 B2 † | 11/2012 | Beasley | |
| 9,125,829 B2 † | 9/2015 | Bonda | |
| 2003/0161793 A1 | 8/2003 | Candau | |
| 2003/0180230 A1 | 9/2003 | Candau | |
| 2004/0247538 A1 | 12/2004 | Wendel et al. | |
| 2005/0008587 A1 | 1/2005 | Schulz et al. | |
| 2009/0068130 A1 † | 3/2009 | Spaulding | |
| 2010/0283015 A1 | 11/2010 | Bonda et al. | |
| 2012/0148512 A1 | 6/2012 | Flösser-Müller | |
| 2013/0028853 A1 * | 1/2013 | Nurse ............... A61K 8/37 424/59 |
| 2013/0142737 A1 | 6/2013 | Schlifkeposchalko et al. | |
| 2013/0251650 A1 | 9/2013 | Winkler et al. | |
| 2018/0296452 A1 † | 10/2018 | Matsui | |

FOREIGN PATENT DOCUMENTS

| | | | |
|---|---|---|---|
| DE | 202008010003 U1 † | 11/2008 | |
| JP | 2013-517250 A | 5/2013 | |
| WO | 2006/034968 A1 | 4/2006 | |
| WO | 2006/114381 A1 | 11/2006 | |

OTHER PUBLICATIONS

International Search Report and Written Opinion received for PCT Patent Application No. PCT/EP2020/056926, mailed on Jun. 8, 2020, 11 pages.
Chaudhury et al., "3-(3,4,5-Trimethoxybenzylidene)-2,4-pentanedione: Design of a novel photostabilizer with in vivo SPF boosting properties and its use in developing broad-spectrum sunscreen formulations," International Journal of Cosmetic Science, vol. 39, Issue 1, Feb. 2017, pp. 25-35.
International Preliminary Report on Patentability received for PCT Patent Application No. PCT/EP2020/056926, mailed on Sep. 30, 2021, 10 pages.
Lhiaubet-Vallet et al., "Filter-filter interactions. Photostabilization, triplet quenching and reactivity with singlet oxygen," Photochemical & Photobiological Science, vol. 9, Issue 4, Jan. 1, 2010, pp. 552-558.
Lim et al., "Clinical Guide to Sunscreens and Photoprotection", Informa Healthcare, 2009, pp. 1-9.
"Anti-Ageing Day Cream Q10+ Refill", Retrieved from the link: "hUp://www.gnpd.com", pp. 1-6.

* cited by examiner
† cited by third party

Primary Examiner — Robert A Wax
Assistant Examiner — Quanglong N Truong
(74) Attorney, Agent, or Firm — Faegre Drinker Biddle & Reath LLP

(57) ABSTRACT

The present invention relates to sunscreen or daily care compositions comprising butyl methoxydibenzoylmethane, at least one UV filter selected from triazine derivatives, at least one photostabilizer selected from butyl octyl salicylate, benzotriazolyl dodecyl p cresol, ethyl hexyl methoxycrylene, polyester-8, diethyl hexyl syringylidenemalonate, trimethoxybenzylidene pentanedione, diethylhexyl 2,6-naphthalate, a fused ring cyanoacrylate derivative and polyester-25, wherein the composition does not comprise octocrylene and ethyl hexyl methoxy cinnamate.

9 Claims, No Drawings

SUNSCREEN COMPOSITIONS COMPRISING BUTYL METHOXYDIBENZOYLMETHANE, TRIAZINE DERIVATIVES AND PHOTOSTABILIZER

CROSS-REFERENCE TO RELATED APPLICATIONS

This application is a national stage application (under 35 U.S.C. § 371) of PCT/EP2020/056926, filed Mar. 13, 2020, which claims benefit of European Application No. 19163171.2, filed Mar. 15, 2019, both of which are incorporated herein by reference in their entirety.

The present invention relates to sunscreen or daily care compositions comprising butyl methoxydibenzoylmethane, at least one UV filter selected from triazine derivatives, at least one photostabilizer selected from butyloctyl salicylate, benzotriazolyl dodecyl p cresol, ethylhexyl methoxycrylene, polyester-8, diethylhexyl syringylidenemalonate, trimethoxybenzylidene pentanedione, diethylhexyl 2,6-naphthalate, a fused ring cyanoacrylate derivative and polyester-25, wherein the composition does not comprise octocrylene and ethylhexyl methoxy cinnamate.

UV radiation causes harmful effects on the human skin. Beside the acute effect of sunburn of the skin, UV radiation is also known to increase the risk of skin cancer. Furthermore, long time exposure to UV-A and UV-B light can cause phototoxic and photo allergenic reactions on the skin and can accelerate skin aging.

To protect the human skin from UV radiation, various sun protecting UV filters (also referred to as UV absorbers) exist including UV-A filter, UV-B filter and broadband filters. These filters are added to sunscreen or cosmetic compositions. The UV filters are either organic or inorganic, particulate or non-particulate compounds, of which all have a high absorption efficacy in the UV-light range. In general, UV light can be divided into UV-A radiation and UV-B radiation. Depending on the position of the absorption maxima, UV-filters are divided into UV-A and UV-B filters. In case an UV-filter absorbs both, UV-A and UV-B light, it is referred to as a broadband absorber.

Since 2006, the EU commission has recommended that all sunscreen or cosmetic compositions should have an UV-A protection factor, which is at least one third of the labelled sun protection factor (SPF), wherein the sun protection factor refers mainly to the UV-B protection.

However, the UV filters known in the prior art, which are used in sunscreen or cosmetic compositions have certain disadvantages. In particular, it is referred to the disadvantage of certain UV filter, which tend to isomerize upon UV irradiation or are destabilized in the presence of other UV filter. As a result, those UV filters lose their protective properties and need to be stabilized in sunscreen or cosmetic compositions. Commonly used stabilizer with UV protective properties are for example octocrylene. However, there exist further compounds, i.e. photostabilizers to stabilize UV filters in sunscreen or daily care compositions. Accordingly there is a need for sunscreen or cosmetic compositions providing an efficient UVA and UVB protection.

Furthermore, it is referred to the disadvantage of certain UV filter, which are frequently under discussion due to their health and environmental concern, although they are approved for being used in sunscreen or cosmetic compositions. UV filter under discussion are for example octocrylene or ethylhexyl methoxy cinnamate. Therefore, there is a need for sunscreen or cosmetic compositions of the daily use, which are efficient for sun protection in the UV-B and UV-A range but free of UV filter under discussion.

WO 2006/114381 discloses the use of benzotriazole derivatives for enhancing the photostability of UV absorber systems further comprising organic UV absorber such as cinnamic acid ester or dibenzoylmethane derivatives.

US 2003/0180230 A1 relates to topically applicable sunscreen compositions, which contain a dibenzoylmethane compound, at least one UV-screening 1,3,5-triazine compound and an photostabilizing amount of at least one UV-screening amino-substituted 2-hydroxybenzophenone.

WO 2006/034968 A1 discloses the use of stabilizing agents to improve the stability of a cosmetic or dermatological composition comprising at least one dibenzoylmethane derivative and at least one amino-substituted 2-hydroxybenzophenone derivative.

US 2003/0161793 A1 refers to topically applicable sunscreen compositions devoid of any p-methylbenzylidene camphor and containing at least one UV-screening dibenzoylmethane compound, and at least one UV screening amino-substituted 2-hydroxybnezophenone.

Therefore, it has been an object of the present invention to provide efficient sunscreen or daily care compositions. It has been another object of the present invention to provide efficient sunscreen or daily care compositions perfectly meeting the consumer's demands with respect to protection performance and convenience upon and after applying the product. In this connection, it has been another object of the present invention to provide sunscreen or daily care compositions, which are free of certain UV filters under discussion. It has been another object of the present invention to provide sunscreen or daily care compositions, which are free of certain critical UV filters under discussion. Further, it has been another object of the present invention to provide compositions, which are suitable for use in sunscreen or daily care compositions in order to enhance the photostability of certain UV filters comprised in the composition, in particular to enhance the photostability of highly effective UV filters comprised in the composition.

It has surprisingly been found that at least one of these objects can be achieved by the sunscreen or daily care composition according to the present invention.

In particular, the inventors of the present application found that the sunscreen or daily care composition according to the present invention provides an efficient UV-A and UV-B protection, nevertheless the composition is free of certain UV filter under discussion, i.e. octocrylene and ethylhexyl methoxy cinnamate. Furthermore, it has surprisingly been found by the inventors of the present application that the sunscreen or daily care composition according to the present invention can be used to enhance the photostability of the at least one UV filter selected from triazine derivatives.

Thus, according to one embodiment, the present invention relates to a sunscreen or daily care composition comprising
  (i) 1-(4-(1,1-dimethylethyl)phenyl)-3-(4-methoxyphenyl) propane-1,3-dione (INCI butyl methoxydibenzoylmethane); and
  (ii) at least one UV filter selected from triazine derivatives; and
  (iii) at least one photostabilizer selected from the group consisting of butyloctyl salicylate, benzotriazolyl dodecyl p cresol, ethylhexyl methoxycrylene, polyester-8, diethylhexyl syringylidenemalonate, trimethoxybenzylidene pentanedione, diethylhexyl 2,6-naphthalate, a fused ring cyanoacrylate derivative, polyester-25 and combinations thereof;

wherein the composition does not comprise ethylhexyl-2-cyano-3,3-diphenyl-acrylate (INCI octocrylene) and 2-ethylhexyl-(2E)-3-(4-methoxyphenyl)acrylate (INCI ethylhexyl methoxy cinnamate).

In a preferred embodiment of said composition, in the sunscreen or daily care composition the at least one UV filter selected from triazine derivatives is selected from the group consisting of soluble triazine derivatives, particulate triazine derivatives and combinations thereof.

In a more preferred embodiment of said composition, in the sunscreen or daily care composition the soluble triazine derivative is selected from the group consisting of 4,4',4"-(1,3,5-triazine-2,4,6-triyltriimino)tris-benzoic acid-tris(2-ethylhexyl)ester (INCI ethylhexyl triazone), 4,4'-[[6-[[4-[[(1,1-dimethylethyl)amino]carbonyl]phenyl]amino]-1,3,5-triazin-2,4-diyl]diimino]bis-benzoic acid-bis(2-ethylhexyl) ester (INCI diethylhexyl-butamidotriazone), 2,4-bis-{[4-(2-ethyl-hexyloxy)-2-hydroxy]-phenyl}-6-(4-methoxyphenyl)-1,3,5 triazine (INCI bis-ethylhexyloxyphenol methoxyphenyl triazine) and combinations thereof.

In another more preferred embodiment of said composition, in the sunscreen or daily care composition the particulate triazine derivative is selected from the group consisting of 2,4,6-tris(biphenyl-4-yl)-1,3,5-triazine (INCI trisbiphenyl triazine), 5,6,5',6'-tetraphenyl-3-3'-(1,4-phenylene)bis(1,2,4-triazine) (INCI phenylene bis-diphenyltriazine) and combinations thereof.

In another preferred embodiment of said composition, the sunscreen or daily care composition is free of any cinnamic acid derivatives.

In another preferred embodiment of said composition, the sunscreen or daily care composition comprises 1-(4-(1,1-dimethylethyl)phenyl)-3-(4-methoxyphenyl)propane-1,3-dione (INCI butyl methoxydibenzoylmethane) in an amount of from 1% to 5% by weight, based on the total weight of the composition.

In another preferred embodiment of said composition, the sunscreen or daily care composition comprises the at least one UV filter selected from triazine derivatives in an amount of from 0.5% to 10% by weight, preferably in an amount of from 0.5% to 5% by weight, based on the total weight of the composition.

In another preferred embodiment of said composition, the sunscreen or daily care composition comprises the at least one photostabilizer in an amount of from 0.5% to 5% by weight, based on the total weight of the composition.

In another preferred embodiment of said composition, the sunscreen or daily care composition is free of parabens.

In another preferred embodiment of said composition, the sunscreen or daily care composition comprises at least one perfume.

In another preferred embodiment of said composition, the sunscreen or daily care composition comprises at least one emollient.

In another aspect the present invention relates to the use of a sunscreen or daily care composition to enhance the photostability of the at least one UV filter selected from triazine derivatives, wherein the composition comprises
(i) 1-(4-(1,1-dimethylethyl)phenyl)-3-(4-methoxyphenyl) propane-1,3-dione (INCI butyl methoxydibenzoylmethane); and
(ii) at least one UV filter selected from triazine derivatives; and
(iii) at least one photostabilizer selected from the group consisting of butyloctyl salicylate, benzotriazolyl dodecyl p cresol, ethylhexyl methoxycrylene, polyester-8, diethylhexyl syringylidenemalonate, trimethoxybenzylidene pentanedione, diethylhexyl 2,6-naphthalate, a fused ring cyanoacrylate derivative, polyester-25 and combinations thereof; and wherein the composition does not comprise ethylhexyl-2-cyano-3,3-diphenyl-acrylate (INCI octocrylene) and 2-ethylhexyl-(2E)-3-(4-methoxyphenyl)acrylate (INCI ethylhexyl methoxy cinnamate).

In a preferred embodiment of said use, in the sunscreen or daily care composition the at least one UV filter selected from triazine derivatives is selected from the group consisting of soluble triazine derivatives, particulate triazine derivatives and combinations thereof.

In a more preferred embodiment of said use, in the sunscreen or daily care composition the soluble triazine derivative is selected from the group consisting of 4,4',4"-(1,3,5-triazine-2,4,6-triyltriimino)tris-benzoic acid-tris(2-ethylhexyl)ester (INCI ethylhexyl triazone), 4,4'-[[6-[[4-[[(1,1-dimethylethyl)amino]carbonyl]phenyl]amino]-1,3,5-triazin-2,4-diyl]diimino]bis-benzoic acid-bis(2-ethylhexyl) ester (INCI diethylhexyl-butamidotriazone), 2,4-bis-{[4-(2-ethyl-hexyloxy)-2-hydroxy]-phenyl}-6-(4-methoxyphenyl)-1,3,5 triazine (INCI bis-ethylhexyloxyphenol methoxyphenyl triazine) and combinations thereof.

In another more preferred embodiment of said use, in the sunscreen or daily care composition the particulate triazine derivative is selected from the group consisting of 2,4,6-tris(biphenyl-4-yl)-1,3,5-triazine (INCI trisbiphenyl triazine), 5,6,5',6'-tetraphenyl-3-3'-(1,4-phenylene)bis(1,2,4-triazine) (INCI phenylene bis-diphenyltriazine) and combinations thereof.

In another preferred embodiment of said use, the sunscreen or daily care composition is free of any cinnamic acid derivatives.

In another preferred embodiment of said use, the sunscreen or daily care composition comprises 1-(4-(1,1-dimethylethyl)phenyl)-3-(4-methoxyphenyl)propane-1,3-dione (INCI butyl methoxydibenzoylmethane) in an amount of from 1% to 5% by weight, based on the total weight of the composition.

In another preferred embodiment of said use, the sunscreen or daily care composition comprises the at least one UV filter selected from triazine derivatives in an amount of from 0.5% to 10% by weight, preferably in an amount of from 0.5% to 5% by weight, based on the total weight of the composition.

In another preferred embodiment of said use, the sunscreen or daily care composition comprises the at least one photostabilizer in an amount of from 0.5% to 5% by weight, based on the total weight of the composition.

In another preferred embodiment of said use, the sunscreen or daily care composition is free of parabens.

In another preferred embodiment of said use, the sunscreen or daily care composition comprises at least one perfume.

In another preferred embodiment of said use, the sunscreen or daily care composition comprises at least one emollient.

Before describing preferred embodiments of the present invention in detail, definitions important for understanding the present invention are given.

As used in this specification and in the appended claims, the singular forms of "a" and "an" also include the respective plurals unless the context clearly dictates otherwise. In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%. It is to be understood that the term "comprising" is not limiting. For the purposes of the present invention, the term "consisting of" is considered to be a preferred embodiment of the term "comprising of". If hereinafter a group is defined to comprise at least a certain number of embodiments, this is meant to also encompass a group, which preferably consists of these embodiments only.

Furthermore, the terms "first", "second", "third" or "(i)", "(ii)", "(iii)", "(iv)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

As used herein the term "free of" in the context that the composition of the present invention is free of a specific compound or group of compounds, which may be combined under a collective term, means that the composition does not comprise said compound or group of compounds in an amount of more than 0.8% by weight, based on the total weight of the composition. Furthermore, it is preferred that the composition according to the present invention does not comprise said compounds or group of compounds in an amount of more than 0.5% by weight, preferably the composition does not comprise said compounds or group of compounds at all. The same definition is applied for the term "does not comprise". Furthermore, it is to be understood that the term "free of" or "does not comprise", in case the composition does not comprise a compound X and a compound Y means that the compositions must be free of both compounds X and Y. In other words, the composition may not contain any compound selected from X and Y.

The term "sunscreen composition" refers to any topical product, which reflects and/or absorbs certain parts of UV radiation. Thus, the term "sunscreen composition" is to be understood as not only including sunscreen compositions, but also any cosmetic compositions that provide UV protection. The term "topical product" refers to a product that is applied to the skin and can refer, e.g., to sprays, lotions, creams, oils, or gels. The sunscreen composition may comprise one or more active agents, e.g., organic or inorganic UV filters, as well as other ingredients or additives, e.g., emulsifiers, emollients, viscosity regulators, stabilizers, preservatives, or fragrances.

The term "daily care composition" refers to any topical product, which reflects and/or absorbs certain parts of UV radiation and is used as an everyday care product for the human body, e.g., for face, body or hair. The daily care composition may comprise one or more active agents, e.g., organic or inorganic UV filters, as well as other ingredients or additives, e.g., emulsifiers, emollients, viscosity regulators, stabilizers, preservatives, or fragrances.

The term "sun protection factor (SPF)" as used herein indicates how well the skin is protected by a sunscreen composition mainly from UV-B radiation. In particular, the factor indicates how much longer the protected skin may be exposed to the sun without getting a sunburn in comparison to untreated skin. For example, if a sunscreen composition with an SPF of 15 is evenly applied to the skin of a person usually getting a sunburn after 10 minutes in the sun, the sunscreen allows the skilled person to stay in the sun 15 times longer. In other words, SPF 15 means that 1/15 of the burning UV radiation will reach the skin, assuming sunscreen is applied evenly at a thick dosage of 2 milligrams per square centimeter ($mg/cm^2$).

The term "UV-filter" as used herein refers to organic or inorganic compounds, which can absorb and/or reflect UV radiation caused by sunlight. UV-filter can be classified based on their UV protection curve as UV-A, UV-B or broadband filters. In the context of the present application, broadband filters may be listed as UV-A filters, as they also provide UV-A protection. In other words, preferred UV-A filters also include broadband filters.

The term "soluble UV filters" refers to UV filters, which have a solubility in the water or oil phase of at least 2% by weight, preferably at least 3% by weight, more preferably at least 5% by weight.

Particulate UV filters can be further divided into organic particulate UV filters and inorganic particulate UV filters. While organic particulate UV filters are based on organic compounds, inorganic particulate UV filters are based on inorganic compounds such as titanium dioxide. In the sunscreen composition, particulate UV filters will be present in particulate form, as their solubility is less than 0.01% by weight, preferably less than 0.05% by weight in the sunscreen composition, i.e. in the water and the cosmetic oils contained therein. Preferably, the particulate UV filters have a particle size $D_N50$ determined by light scattering of less than 2000 nm, preferably less than 1000 nm, wherein $D_N50$ refers to the particle size value, where half of the population lies below this value, and half of the population lies above this value, i.e. the median value of the particle size volume distribution.

1-(4-(1,1-dimethylethyl)phenyl)-3-(4-methoxyphenyl) propane-1,3-dione (INCI butyl methoxydibenzoylmethane) is a soluble organic UV-A filter. It absorbs UV-A radiation in the range of from 320 nm to 400 nm with an absorption maximum at 357 nm.

Ethylhexyl-2-cyano-3,3-diphenyl-acrylate (INCI octocrylene) is an oil soluble organic UV-B filter with an absorption maximum at 302 nm. It provides a broad UV-B absorbance and is known to be an efficient stabilizer for photounstable UV filters. Octocrylene is sold by BASF under the tradename Uvinul® N 539 T.

2-Ethylhexyl-(2E)-3-(4-methoxyphenyl)acrylate (INCI ethylhexyl methoxy cinnamate) is an odorless and colorless UV-B filter with an absorption maximum at 310 nm. It is a good solvent for other crystalline UV filters. Ethylhexyl methoxy cinnamate is sold under the tradename Uvinul® MC 80 by BASF.

The term "photostabilizer" refers to organic compounds, which prevent UV filters from undergoing degradation processes upon UV radiation or by destabilization of the presence of other compounds, which can be for example another UV filter. Photostabilizer either protect the UV filter by structural or geometrical means, or by dissipating energy from the UV filter in order to reduce the possibility of destabilization.

Butyloctyl salicylate is a synthetically produced ester of salicylic acid and 2-butyloctanol. It is sold under the trade name HallBrite BHB® by Hallstar.

Benzotriazolyl dodecyl p-cresol is sold by BASF under the trade name Tinogard® TL.

Ethylhexyl methoxycrylene is sold by Hallstar under the trade name SolaStay® S1.

Polyester-8 is a copolymer of adipic acid and neopentyl glycol terminated with cyanodiphenyl propenoic acid with an average MW of approximately 1900 daltons. It is sold under the trade name Polycrylene® by Hallstar.

Diethylhexyl syringylidenemalonate is a stabilizer for light sensitive ingredients. It is sold by Merck KGaA under the trade name Oxynex® ST Liquid.

Trimethoxybenzylidene pentanedione functions as a triplet state quencher. It is sold under the trade name Synoxyl HSS by Sytheon.

Diethylhexyl 2,6-naphthalate is used as a photostabilizer and emollient. It is sold by Symrise under the trade name Corapan TQ.

Polyester-25 is a bis-methoxycrylene/octyldodecyl adipic acid/methylpropanediol copolymer. It is sold by Hallstar under the trade name SolaStay® P1.

The term "fused-ring cyanoacrylate derivative" refers to the compound "Micah" provided by the company Hallstar. The compound is based on the following structural formula

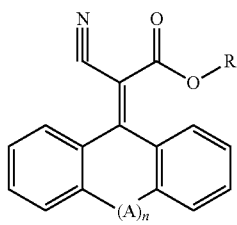

In the context of the present application the compound "Micah" belongs to the group of photostabilizer.

The term "paraben" refers to a class of preservatives used in cosmetic and pharmaceutical compositions. They are commonly used due to their bactericidal and fungicidal properties. The chemical structure of parabens is based on parahydroxybenzoates or esters of parahydroxybenzoic acid, e.g. methylparaben, ethylparaben, propylparaben, butylparaben or heptylparaben.

The term "emollient" relates to cosmetic preparations used for protecting, moisturizing and lubricating the skin. The word emollient is derived from the Latin word mollire, to soften. In general, emollients prevent evaporation of water from the skin by forming an occlusive coating.

The definition of "broadband" protection (also referred to as broad-spectrum or broad protection) is based on the "critical wavelength". For broadband coverage, UV-B and UV-A protection must be provided. According to the US requirements, a critical wavelength of at least 370 nm is required for achieving broad spectrum protection. Furthermore, it is recommended by the European Commission that all sunscreen or cosmetic compositions should have an UVA protection factor, which is at least one third of the labelled sun protection factor (SPF), e.g. if the sunscreen composition has an SPF of 30 the UVA protection factor has to be at least 10.

Preferred embodiments regarding the sunscreen or daily care composition according to the present application as well as the use of said composition are described hereinafter. It is to be understood that the preferred embodiments of the invention are preferred alone or in combination with each other.

As indicated above, the present invention relates in one embodiment to a sunscreen or daily care composition comprising
(i) 1-(4-(1,1-dimethylethyl)phenyl)-3-(4-methoxyphenyl) propane-1,3-dione (INCI butyl methoxydibenzoylmethane); and
(ii) at least one UV filter selected from triazine derivatives; and
(iii) at least one photostabilizer selected from the group consisting of butyloctyl salicylate, benzotriazolyl dodecyl p cresol, ethylhexyl methoxycrylene, polyester-8, diethylhexyl syringylidenemalonate, trimethoxybenzylidene pentanedione, diethylhexyl 2,6-naphthalate, a fused ring cyanoacrylate derivative, polyester-25 and combinations thereof;
wherein the composition does not comprise ethylhexyl-2-cyano-3,3-diphenyl-acrylate (INCI octocrylene) and 2-ethylhexyl-(2E)-3-(4-methoxyphenyl)acrylate (INCI ethylhexyl methoxy cinnamate).

In connection with the present invention, the following preferences regarding the sunscreen composition are relevant.

In one embodiment of the present invention, the sunscreen or daily care composition comprises
(i) 1-(4-(1,1-dimethylethyl)phenyl)-3-(4-methoxyphenyl) propane-1,3-dione (INCI butyl methoxydibenzoylmethane); and
(ii) at least one UV filter selected from triazine derivatives; and
(iii) at least one photostabilizer selected from the group consisting of butyloctyl salicylate, benzotriazolyl dodecyl p cresol, ethylhexyl methoxycrylene, polyester-8, diethylhexyl syringylidenemalonate, trimethoxybenzylidene pentanedione, diethylhexyl 2,6-naphthalate, a fused ring cyanoacrylate derivative, polyester-25 and combinations thereof;
wherein the composition does not comprise ethylhexyl-2-cyano-3,3-diphenyl-acrylate (INCI octocrylene) and 2-ethylhexyl-(2E)-3-(4-methoxyphenyl)acrylate (INCI ethylhexyl methoxy cinnamate).

In another embodiment of the present invention, the sunscreen or daily care composition as defined above is free of any cinnamic acid derivatives. In this connection, it is to be understood that cinnamic acid derivatives refers to any derivative deriving from the structural formula of cinnamic acid ester. In particular, it is referred to the cinnamic acid derivatives 2-ethylhexyl 4-methoxycinnamte and isoamyl-p-methoxycinnamate, which are excluded from the sunscreen or daily care composition according to the present invention.

In yet another embodiment of the present invention, the sunscreen or daily care composition is free of parabens. In this connection, it is to be understood that parabens are also known by the synonyms parahydroxybenzoate, oxybenzoates, oxybenzoic acid, hydroxybenzoic acid, and hydroxybenzoate, which are also excluded from the sunscreen or daily care composition according to the present invention.

In yet another embodiment of the present invention, the sunscreen or daily care composition as defined above is free of phenoxyethanol.

In connection with the above embodiments, it is to be understood that free of means that the composition does not comprise the above-defined compounds or substances. In particular, it is to be understood that the composition does not comprise the above-defined compounds or substances in an amount of more than 0.8% by weight respectively, based on the total weight of the composition. Furthermore, it is to be understood that the composition does not comprise the above-defined compounds or substances in an amount of more than 0.5% by weight respectively.

In a preferred embodiment of the present invention, the sunscreen or daily care composition as defined above does not comprise each of the compounds or substances as defined above at all.

In connection with the above embodiments, it is further to be understood that the sunscreen or daily care composition as defined above according to the present invention is free of the substances as defined above and also the combinations of the compounds or substances as defined above, i.e. the composition according to the present invention is free of any cinnamic acid derivative, parabens and phenoxyethanol.

In this connection, it is to be understood that free of means that the composition does not comprise the above-defined combination of substances in an overall amount of more than 0.8% by weight, based on the total weight of the composition. Furthermore, it is preferred that the composition does not comprise the above-defined combination of substances in an overall amount of more than 0.5% by weight.

In a preferred embodiment of the present invention, the sunscreen or daily care composition as defined above does not comprise the above-defined combination of substances at all.

Furthermore, in connection with the above preferred embodiments, it is to be understood that the sunscreen or daily care composition according to the present invention is free of the substances as defined above or combinations thereof in addition to octocrylene and ethylhexyl methoxycinnamate.

In connection with the present invention, the following preferences regarding the UV filters and photostabilizer are relevant in connection with the above listed embodiments.

In one embodiment of the present invention, the sunscreen or daily care composition as defined above comprises
(i) 1-(4-(1,1-dimethylethyl)phenyl)-3-(4-methoxyphenyl) propane-1,3-dione (INCI butyl methoxydibenzoylmethane); and
(ii) at least one UV filter selected from triazine derivatives; and
(iii) at least one photostabilizer selected from the group consisting of butyloctyl salicylate, benzotriazolyl dodecyl p cresol, ethylhexyl methoxycrylene, polyester-8, diethylhexyl syringylidenemalonate, trimethoxybenzylidene pentanedione, diethylhexyl 2,6-naphthalate, a fused ring cyanoacrylate derivative, polyester-25 and combinations thereof;
wherein the composition does not comprise ethylhexyl-2-cyano-3,3-diphenyl-acrylate (INCI octocrylene) and 2-ethylhexyl-(2E)-3-(4-methoxyphenyl)acrylate (INCI ethylhexyl methoxy cinnamate).

In a preferred embodiment of the present invention, the sunscreen or daily care composition as defined above comprises the at least one UV filter selected from triazine derivatives, wherein the "at least one UV filter selected from triazine derivatives" may preferably refer to from 1 to 3 UV filter selected from triazine derivatives.

In another preferred embodiment of the present invention, the sunscreen or daily care composition as defined above comprises the at least one UV filter selected from triazine derivatives selected from the group consisting of soluble triazine derivatives, particulate triazine derivatives and combinations thereof.

In a more preferred embodiment of the present invention, the soluble triazine derivative is selected from the group consisting of 4,4',4"-(1,3,5-triazine-2,4,6-triyltriimino)tris-benzoic acid-tris(2-ethylhexyl)ester (INCI ethylhexyl triazone), 4,4'-[[6-[[4-[[(1,1-dimethylethyl)amino]carbonyl]phenyl]amino]-1,3,5-triazin-2,4-diyl]diimino]bis-benzoic acid-bis(2-ethylhexyl)ester (INCI diethylhexyl-butamidotriazone), 2,4-bis-{[4-(2-ethyl-hexyloxy)-2-hydroxy]-phenyl}-6-(4-methoxyphenyl)-1,3,5 triazine (INCI bis-ethylhexyloxyphenol methoxyphenyl triazine) and combinations thereof.

If in the sunscreen or daily care composition combinations of 2 soluble triazine derivatives are present, the following combinations are individually preferred:
ethylhexyl triazone and diethylhexyl-butamidotriazone;
ethylhexyl triazone and bis-ethylhexyloxyphenol methoxyphenyl triazine; and
diethylhexyl-butamidotriazone and bis-ethylhexyloxyphenol methoxyphenyl triazine.

In another more preferred embodiment of the present invention, the particulate triazine derivative is selected from the group consisting of 2,4,6-tris(biphenyl-4-yl)-1,3,5-triazine (INCI trisbiphenyl triazine), 5,6,5',6'-tetraphenyl-3-3'-(1,4-phenylene)bis(1,2,4-triazine) (INCI phenylene bis-diphenyltriazine) and combinations thereof.

If in the sunscreen or daily care composition the combination of 2 particulate triazine derivatives is present, the combination of trisbiphenyl triazine and phenylene bis-diphenyltriazine is individually preferred.

In connection with the above preferred embodiments, it is to be understood that if in the sunscreen or daily care composition the combination of 2 triazine derivatives is present, also a combination of one soluble triazine derivative and one particulate triazine derivative is part of the invention. Thus, the following combinations are individually preferred:
ethylhexyl triazone and trisbiphenyl triazine;
ethylhexyl triazone and phenylene bis-diphenyltriazine;
diethylhexyl-butamidotriazone and trisbiphenyl triazine;
diethylhexyl-butamidotriazone and phenylene bis-diphenyltriazine;
bis-ethylhexyloxyphenol methoxyphenyl triazine and trisbiphenyl triazine; and
bis-ethylhexyloxyphenol methoxyphenyl triazine and phenylene bis-diphenyltriazine.

If the sunscreen or daily care composition comprises a combination of 3 triazine derivatives selected from soluble triazine derivatives and particulate triazine derivatives the following combinations are individually preferred:
ethylhexyl triazone, trisbiphenyl triazine and bis-ethylhexyloxyphenol methoxyphenyl triazine;
diethylhexyl-butamidotriazone, trisbiphenyl triazine bis-ethylhexyloxyphenol methoxyphenyl triazine.

If the sunscreen or daily care composition comprises a combination of 4 triazine derivatives selected from soluble triazine derivatives and particulate triazine derivatives the combination of ethylhexyl triazone, trisbiphenyl triazine, diethylhexyl-butamidotriazone and bis-ethylhexyloxyphenol methoxyphenyl triazine is individually preferred.

In a preferred embodiment of the present invention, the sunscreen or daily care composition comprises the least one UV filter selected from triazine derivatives as defined above in an amount of from 0.5% to 10% by weight, preferably in an amount of from 0.5% to 5% by weight, based on the total weight of the composition. It is to be understood that these amounts refer to each individual UV filter selected from triazine derivatives in the sunscreen or daily care composition. Thus, each individual UV filter selected from triazine derivatives as defined above in the sunscreen or daily care composition is preferably present in an amount of from 0.5% to 10% by weight, preferably in an amount of from 0.5% to 5% by weight, based on the total weight of the composition. If two or more UV filter selected from triazine derivatives are present in the sunscreen or daily care composition as defined above, the overall amount of the UV filters selected from triazine derivatives as defined above may preferably be in the range of from 1% to 15% by weight, preferably from 1.5% to 8% by weight, based on the total weight of the sunscreen or daily care composition.

In another preferred embodiment of the present invention, the sunscreen or daily care composition as defined above comprises the at least one photostabilizer, wherein the "at least one photostabilizer" may preferably refer to from 1 to 3 photostabilizer. In a more preferred embodiment the "at least one photostabilizer" may preferably refer to 1 or 2 photostabilizer.

In this connection it is to be understood, that the at least one photostabilizer is selected from the group consisting of butyloctyl salicylate, benzotriazolyl dodecyl p cresol, ethylhexyl methoxycrylene, polyester-8, diethylhexyl syringylidenemalonate, trimethoxybenzylidene pentanedione, diethylhexyl 2,6-naphthalate, a fused ring cyanoacrylate derivative, polyester-25 and combinations thereof.

In a preferred embodiment of the present invention, in the sunscreen or daily care composition as defined above, the at least one photostabilizer is selected from the group consisting of benzotriazolyl dodecyl p cresol, ethylhexyl methoxycrylene, polyester-8, diethylhexyl syringylidenemalonate, trimethoxybenzylidene pentanedione, a fused ring cyanoacrylate derivative, polyester-25 and combinations thereof.

If the combination of 2 photostabilizer is present in the sunscreen or daily care composition the following combinations are individually preferred:

butyloctyl salicylate and benzotriazolyl dodecyl p cresol;
butyloctyl salicylate and ethylhexyl methoxycrylene;
butyloctyl salicylate and polyester-8;
butyloctyl salicylate and diethylhexyl syringylidenemalonate;
butyloctyl salicylate and trimethoxybenzylidene pentanedione;
butyloctyl salicylate and diethylhexyl 2,6-naphthalate;
butyloctyl salicylate and a fused ring cyanoacrylate derivative;
butyloctyl salicylate and polyester-25;
benzotriazolyl dodecyl p cresol and ethylhexyl methoxycrylene;
benzotriazolyl dodecyl p cresol and polyester-8;
benzotriazolyl dodecyl p cresol and diethylhexyl syringylidenemalonate;
benzotriazolyl dodecyl p cresol and trimethoxybenzylidene pentanedione;
benzotriazolyl dodecyl p cresol and diethylhexyl 2,6-naphthalate;
benzotriazolyl dodecyl p cresol and a fused ring cyanoacrylate derivative;
benzotriazolyl dodecyl p cresol and polyester-25;
ethylhexyl methoxycrylene and polyester-8;
ethylhexyl methoxycrylene and diethylhexyl syringylidenemalonate;
ethylhexyl methoxycrylene and trimethoxybenzylidene pentanedione;
ethylhexyl methoxycrylene and diethylhexyl 2,6-naphthalate;
ethylhexyl methoxycrylene and a fused ring cyanoacrylate derivative;
ethylhexyl methoxycrylene and polyester-25;
polyester-8 and diethylhexyl syringylidenemalonate;
polyester-8 and trimethoxybenzylidene pentanedione;
polyester-8 and diethylhexyl 2,6-naphthalate;
polyester-8 and a fused ring cyanoacrylate derivative;
polyester-8 and polyester-25;
diethylhexyl syringylidenemalonate and trimethoxybenzylidene pentanedione;
diethylhexyl syringylidenemalonate and diethylhexyl 2,6-naphthalate;
diethylhexyl syringylidenemalonate and a fused ring cyanoacrylate derivative;
diethylhexyl syringylidenemalonate and polyester-25;
trimethoxybenzylidene pentanedione and diethylhexyl 2,6-naphthalate;
trimethoxybenzylidene pentanedione and a fused ring cyanoacrylate derivative;
trimethoxybenzylidene pentanedione and polyester-25;
diethylhexyl 2,6-naphthalate and a fused ring cyanoacrylate derivative;
diethylhexyl 2,6-naphthalate and polyester-25; and
a fused ring cyanoacrylate derivative and polyester-25.

In a preferred embodiment of the present invention, the sunscreen or daily care composition comprises the least one photostabilizer as defined above in an amount of from 0.5% to 5% by weight, based on the total weight of the composition. It is to be understood that these amounts refer to each individual photostabilizer in the sunscreen or daily care composition. Thus, each individual photostabilizer as defined above in the sunscreen or daily care composition is preferably present in an amount of from 0.5% to 5% by weight, based on the total weight of the composition. If two or more photostabilizer are present in the sunscreen or daily care composition as defined above, the overall amount of the photostabilizer as defined above may preferably be in the range of from 1% to 10% by weight, based on the total weight of the sunscreen or daily care composition.

In a particularly preferred embodiment of the present invention, the following compositions are individually preferred in connection with the above listed embodiments of the present invention.

In one particularly preferred embodiment, the sunscreen or daily care composition comprises
(i) butyl methoxydibenzoylmethane; and
(ii) ethylhexyl triazone; and
(iii) butyloctyl salicylate;
wherein the composition does not comprise octocrylene and ethylhexyl methoxy cinnamate.

In another particularly preferred embodiment, the sunscreen or daily care composition comprises
(i) butyl methoxydibenzoylmethane; and
(ii) diethylhexyl-butamidotriazone; and
(iii) butyloctyl salicylate;
wherein the composition does not comprise octocrylene and ethylhexyl methoxy cinnamate.

In yet another particularly preferred embodiment, the sunscreen or daily care composition comprises
(i) butyl methoxydibenzoylmethane; and
(ii) bis-ethylhexyloxyphenol methoxyphenyl triazine; and
(iii) butyloctyl salicylate;
wherein the composition does not comprise octocrylene and ethylhexyl methoxy cinnamate.

In yet another particularly preferred embodiment, the sunscreen or daily care composition comprises
(i) butyl methoxydibenzoylmethane; and
(ii) trisbiphenyl triazine; and
(iii) butyloctyl salicylate;
wherein the composition does not comprise octocrylene and ethylhexyl methoxy cinnamate.

In yet another particularly preferred embodiment, the sunscreen or daily care composition comprises
(i) butyl methoxydibenzoylmethane; and
(ii) phenylene bis-diphenyltriazine; and
(iii) butyloctyl salicylate;
wherein the composition does not comprise octocrylene and ethylhexyl methoxy cinnamate.

In yet another particularly preferred embodiment, the sunscreen or daily care composition comprises
(i) butyl methoxydibenzoylmethane; and
(ii) ethylhexyl triazone; and
(iii) benzotriazolyl dodecyl p cresol;
wherein the composition does not comprise octocrylene and ethylhexyl methoxy cinnamate.

In another particularly preferred embodiment, the sunscreen or daily care composition comprises
(i) butyl methoxydibenzoylmethane; and
(ii) diethylhexyl-butamidotriazone; and
(iii) benzotriazolyl dodecyl p cresol;
wherein the composition does not comprise octocrylene and ethylhexyl methoxy cinnamate.

In yet another particularly preferred embodiment, the sunscreen or daily care composition comprises
(i) butyl methoxydibenzoylmethane; and
(ii) bis-ethylhexyloxyphenol methoxyphenyl triazine; and
(iii) benzotriazolyl dodecyl p cresol;
wherein the composition does not comprise octocrylene and ethylhexyl methoxy cinnamate.

In yet another particularly preferred embodiment, the sunscreen or daily care composition comprises
(i) butyl methoxydibenzoylmethane; and
(ii) trisbiphenyl triazine; and
(iii) benzotriazolyl dodecyl p cresol;
wherein the composition does not comprise octocrylene and ethylhexyl methoxy cinnamate.

In yet another particularly preferred embodiment, the sunscreen or daily care composition comprises
(i) butyl methoxydibenzoylmethane; and
(ii) phenylene bis-diphenyltriazine; and
(iii) benzotriazolyl dodecyl p cresol;
wherein the composition does not comprise octocrylene and ethylhexyl methoxy cinnamate.

In yet another particularly preferred embodiment, the sunscreen or daily care composition comprises
(i) butyl methoxydibenzoylmethane; and
(ii) ethylhexyl triazone; and
(iii) ethylhexyl methoxycrylene;
wherein the composition does not comprise octocrylene and ethylhexyl methoxy cinnamate.

In yet another particularly preferred embodiment, the sunscreen or daily care composition comprises
(i) butyl methoxydibenzoylmethane; and
(ii) diethylhexyl-butamidotriazone; and
(iii) ethylhexyl methoxycrylene;
wherein the composition does not comprise octocrylene and ethylhexyl methoxy cinnamate.

In yet another particularly preferred embodiment, the sunscreen or daily care composition comprises
(i) butyl methoxydibenzoylmethane; and
(ii) bis-ethylhexyloxyphenol methoxyphenyl triazine; and
(iii) ethylhexyl methoxycrylene;
wherein the composition does not comprise octocrylene and ethylhexyl methoxy cinnamate.

In yet another particularly preferred embodiment, the sunscreen or daily care composition comprises
(i) butyl methoxydibenzoylmethane; and
(ii) trisbiphenyl triazine; and
(iii) ethylhexyl methoxycrylene;
wherein the composition does not comprise octocrylene and ethylhexyl methoxy cinnamate.

In yet another particularly preferred embodiment, the sunscreen or daily care composition comprises
(i) butyl methoxydibenzoylmethane; and
(ii) phenylene bis-diphenyltriazine; and
(iii) ethylhexyl methoxycrylene;
wherein the composition does not comprise octocrylene and ethylhexyl methoxy cinnamate.

In yet another particularly preferred embodiment, the sunscreen or daily care composition comprises
(i) butyl methoxydibenzoylmethane; and
(ii) ethylhexyl triazone; and
(iii) polyester-8;
wherein the composition does not comprise octocrylene and ethylhexyl methoxy cinnamate.

In another particularly preferred embodiment, the sunscreen or daily care composition comprises
(i) butyl methoxydibenzoylmethane; and
(ii) diethylhexyl-butamidotriazone; and
(iii) polyester-8;
wherein the composition does not comprise octocrylene and ethylhexyl methoxy cinnamate.

In yet another particularly preferred embodiment, the sunscreen or daily care composition comprises
(i) butyl methoxydibenzoylmethane; and
(ii) bis-ethylhexyloxyphenol methoxyphenyl triazine; and
(iii) polyester-8;
wherein the composition does not comprise octocrylene and ethylhexyl methoxy cinnamate.

In yet another particularly preferred embodiment, the sunscreen or daily care composition comprises
(i) butyl methoxydibenzoylmethane; and
(ii) trisbiphenyl triazine; and
(iii) polyester-8;
wherein the composition does not comprise octocrylene and ethylhexyl methoxy cinnamate.

In yet another particularly preferred embodiment, the sunscreen or daily care composition comprises
(i) butyl methoxydibenzoylmethane; and
(ii) phenylene bis-diphenyltriazine; and
(iii) polyester-8;
wherein the composition does not comprise octocrylene and ethylhexyl methoxy cinnamate.

In yet another particularly preferred embodiment, the sunscreen or daily care composition comprises
(i) butyl methoxydibenzoylmethane; and
(ii) ethylhexyl triazone; and
(iii) diethylhexyl syringylidenemalonate;
wherein the composition does not comprise octocrylene and ethylhexyl methoxy cinnamate.

In another particularly preferred embodiment, the sunscreen or daily care composition comprises
(i) butyl methoxydibenzoylmethane; and
(ii) diethylhexyl-butamidotriazone; and
(iii) diethylhexyl syringylidenemalonate;
wherein the composition does not comprise octocrylene and ethylhexyl methoxy cinnamate.

In yet another particularly preferred embodiment, the sunscreen or daily care composition comprises
(i) butyl methoxydibenzoylmethane; and
(ii) bis-ethylhexyloxyphenol methoxyphenyl triazine; and
(iii) diethylhexyl syringylidenemalonate;

wherein the composition does not comprise octocrylene and ethylhexyl methoxy cinnamate.

In yet another particularly preferred embodiment, the sunscreen or daily care composition comprises
(i) butyl methoxydibenzoylmethane; and
(ii) trisbiphenyl triazine; and
(iii) diethylhexyl syringylidenemalonate;
wherein the composition does not comprise octocrylene and ethylhexyl methoxy cinnamate.

In yet another particularly preferred embodiment, the sunscreen or daily care composition comprises
(i) butyl methoxydibenzoylmethane; and
(ii) phenylene bis-diphenyltriazine; and
(iii) diethylhexyl syringylidenemalonate;
wherein the composition does not comprise octocrylene and ethylhexyl methoxy cinnamate.

In yet another particularly preferred embodiment, the sunscreen or daily care composition comprises
(i) butyl methoxydibenzoylmethane; and
(ii) ethylhexyl triazone; and
(iii) trimethoxybenzylidene pentanedione;
wherein the composition does not comprise octocrylene and ethylhexyl methoxy cinnamate.

In another particularly preferred embodiment, the sunscreen or daily care composition comprises
(i) butyl methoxydibenzoylmethane; and
(ii) diethylhexyl-butamidotriazone; and
(iii) trimethoxybenzylidene pentanedione;
wherein the composition does not comprise octocrylene and ethylhexyl methoxy cinnamate.

In yet another particularly preferred embodiment, the sunscreen or daily care composition comprises
(i) butyl methoxydibenzoylmethane; and
(ii) bis-ethylhexyloxyphenol methoxyphenyl triazine; and
(iii) trimethoxybenzylidene pentanedione;
wherein the composition does not comprise octocrylene and ethylhexyl methoxy cinnamate.

In yet another particularly preferred embodiment, the sunscreen or daily care composition comprises
(i) butyl methoxydibenzoylmethane; and
(ii) trisbiphenyl triazine; and
(iii) trimethoxybenzylidene pentanedione;
wherein the composition does not comprise octocrylene and ethylhexyl methoxy cinnamate.

In yet another particularly preferred embodiment, the sunscreen or daily care composition comprises
(i) butyl methoxydibenzoylmethane; and
(ii) phenylene bis-diphenyltriazine; and
(iii) trimethoxybenzylidene pentanedione;
wherein the composition does not comprise octocrylene and ethylhexyl methoxy cinnamate.

In yet another particularly preferred embodiment, the sunscreen or daily care composition comprises
(i) butyl methoxydibenzoylmethane; and
(ii) ethylhexyl triazone; and
(iii) diethylhexyl 2,6-naphthalate;
wherein the composition does not comprise octocrylene and ethylhexyl methoxy cinnamate.

In another particularly preferred embodiment, the sunscreen or daily care composition comprises
(i) butyl methoxydibenzoylmethane; and
(ii) diethylhexyl-butamidotriazone; and
(iii) diethylhexyl 2,6-naphthalate;
wherein the composition does not comprise octocrylene and ethylhexyl methoxy cinnamate.

In yet another particularly preferred embodiment, the sunscreen or daily care composition comprises
(i) butyl methoxydibenzoylmethane; and
(ii) bis-ethylhexyloxyphenol methoxyphenyl triazine; and
(iii) diethylhexyl 2,6-naphthalate;
wherein the composition does not comprise octocrylene and ethylhexyl methoxy cinnamate.

In yet another particularly preferred embodiment, the sunscreen or daily care composition comprises
(i) butyl methoxydibenzoylmethane; and
(ii) trisbiphenyl triazine; and
(iii) diethylhexyl 2,6-naphthalate;
wherein the composition does not comprise octocrylene and ethylhexyl methoxy cinnamate.

In yet another particularly preferred embodiment, the sunscreen or daily care composition comprises
(i) butyl methoxydibenzoylmethane; and
(ii) phenylene bis-diphenyltriazine; and
(iii) diethylhexyl 2,6-naphthalate;
wherein the composition does not comprise octocrylene and ethylhexyl methoxy cinnamate.

In yet another particularly preferred embodiment, the sunscreen or daily care composition comprises
(i) butyl methoxydibenzoylmethane; and
(ii) ethylhexyl triazone; and
(iii) a fused ring cyanoacrylate derivative;
wherein the composition does not comprise octocrylene and ethylhexyl methoxy cinnamate.

In another particularly preferred embodiment, the sunscreen or daily care composition comprises
(i) butyl methoxydibenzoylmethane; and
(ii) diethylhexyl-butamidotriazone; and
(iii) a fused ring cyanoacrylate derivative;
wherein the composition does not comprise octocrylene and ethylhexyl methoxy cinnamate.

In yet another particularly preferred embodiment, the sunscreen or daily care composition comprises
(i) butyl methoxydibenzoylmethane; and
(ii) bis-ethylhexyloxyphenol methoxyphenyl triazine; and
(iii) a fused ring cyanoacrylate derivative;
wherein the composition does not comprise octocrylene and ethylhexyl methoxy cinnamate.

In yet another particularly preferred embodiment, the sunscreen or daily care composition comprises
(i) butyl methoxydibenzoylmethane; and
(ii) trisbiphenyl triazine; and
(iii) a fused ring cyanoacrylate derivative;
wherein the composition does not comprise octocrylene and ethylhexyl methoxy cinnamate.

In yet another particularly preferred embodiment, the sunscreen or daily care composition comprises
(i) butyl methoxydibenzoylmethane; and
(ii) phenylene bis-diphenyltriazine; and
(iii) a fused ring cyanoacrylate derivative;
wherein the composition does not comprise octocrylene and ethylhexyl methoxy cinnamate.

In yet another particularly preferred embodiment, the sunscreen or daily care composition comprises
(i) butyl methoxydibenzoylmethane; and
(ii) ethylhexyl triazone; and
(iii) polyester-25;
wherein the composition does not comprise octocrylene and ethylhexyl methoxy cinnamate.

In another particularly preferred embodiment, the sunscreen or daily care composition comprises
(i) butyl methoxydibenzoylmethane; and
(ii) diethylhexyl-butamidotriazone; and
(iii) polyester-25;

wherein the composition does not comprise octocrylene and ethylhexyl methoxy cinnamate.

In yet another particularly preferred embodiment, the sunscreen or daily care composition comprises
(i) butyl methoxydibenzoylmethane; and
(ii) bis-ethylhexyloxyphenol methoxyphenyl triazine; and
(iii) polyester-25;
wherein the composition does not comprise octocrylene and ethylhexyl methoxy cinnamate.

In yet another particularly preferred embodiment, the sunscreen or daily care composition comprises
(i) butyl methoxydibenzoylmethane; and
(ii) trisbiphenyl triazine; and
(iii) polyester-25;
wherein the composition does not comprise octocrylene and ethylhexyl methoxy cinnamate.

In yet another particularly preferred embodiment, the sunscreen or daily care composition comprises
(i) butyl methoxydibenzoylmethane; and
(ii) phenylene bis-diphenyltriazine; and
(iii) polyester-25;
wherein the composition does not comprise octocrylene and ethylhexyl methoxy cinnamate.

In another preferred embodiment of the present invention, the sunscreen or daily care composition comprises at least one further UV filter. In this connection, it is to be understood that the at least one further UV filter is a water soluble UV filter selected from the group consisting of [(3Z)-3-[[4-[(Z)-[7,7-dimethyl-2-oxo-1-(sulfomethyl)-3-bicyclo[2.2.1]heptanylidene]methyl]phenyl]methylidene]-7,7-dimethyl-2-oxo-1-bicyclo[2.2.1]heptanyl]methanesulfonic acid (INCI terephthalylidene dicamphor sulfonic acid), disodium phenyl dibenzimidazole tetrasulfonate, 2-phenylbenzimidazol-5-sulfonic acid and combinations thereof.

In a particularly preferred embodiment of the present invention, the at least one further water soluble UV filter is 2-phenylbenzimidazol-5-sulfonic acid.

In another preferred embodiment of the present invention, the sunscreen or daily care composition comprises 1-(4-(1,1-dimethylethyl)phenyl)-3-(4-methoxyphenyl)propane-1,3-dione (INCI butyl methoxydibenzoylmethane) in an amount of from 1% to 5% by weight, based on the total weight of the composition.

In connection with the above preferred embodiments, it is to be understood that the total weight of the sunscreen or daily care composition refers to the sunscreen or daily care composition as defined above, wherein the sunscreen composition may comprise at least one additive.

In one embodiment, the at least one additive is selected from the group consisting of emulsifier, emollients, viscosity regulators (thickeners), sensory enhancers, adjuvants, preservatives, and combinations thereof.

Preferred emulsifiers include
glucose derivatives such as cetearyl glucoside, arachidyl glucoside, lauryl glucoside, polyglyceryl-3 methylglucose distearate, methyl glucose sesquistearate;
sucrose derivative such as sucrose polystearate, sucrose palmitate;
sorbitol derivatives such as polysorbate-n, PEG-10 sorbitan laurate;
fatty alcohol polyglycolethers and fatty acid polyglycolethers such as ceteareth-20, beheneth-25, steareth-2, PEG-100 stearate;
glycerides of fatty acids such as glyceryl stearate, glyceryl oleate;
glumatic acid derivatives such as sodium stearoyl glutamate;
sulfosuccinic acid derivatives such as disodium cetearyl sulfosuccinate;
phosphoric acid derivatives such as potassium cetyl phosphate;
fatty acid esters of polyglyceryl such as polyglyceryl-3-diisostearate, polyglyceryl-2-dipolyhydroxystearate;
oxyalkenylated organomodified silicone/polysiloxane/polyalkyl/polyether copolymers and derivatives.

Preferred thickeners include
fatty alcohols such as cetyl alcohol, cetearyl alcohol, stearyl alcohol;
fatty acids such as stearic acid;
fatty acid esters such as myristyl stearate;
waxes such as beeswax, carnauba wax, microcrystalline wax, ceresin, ozocerite;
polysaccharides or derivatives such as xanthan gum, guar gum, agar gum, alginates, gellan gum, carraghenan;
polyacrylates or homopolymers of reticulated acrylic acids or polyacrylamides such as carbomers, acrylate copolymers, acrylate/$C_{10}$-$C_{30}$-alkyl acrylate crosspolymer, acrylate/beheneth-25 methacrylate copolymer;
silicate derivatives such as magnesium silicates;
cellulose derivatives such as hydroxypropyl cellulose.

Preferred sensory enhancers include
polyamide derivatives such as nylon-12;
polymethyl methacrylates;
silica;
mica;
polymethylsilsesquioxane;
polyethylene;
starch derivatives such as aluminum starch octenylsuccinate;
dimethicone derivatives;
boron nitride;
HDI/trimethylol hexyllactone crosspolymer.

Preferred adjuvants include
tocopherol derivatives;
retinol derivatives;
ascorbic acid derivatives;
bisabolol;
allantoin;
panthenol;
chelating agents (EDTA, EDDS, EGTA, phytic acid, piroctone olamine);
ethylhexyl glycerin;
caprylyl glycol;
hydroxyacetophenone;
caprylhydroxymic acid;
propellants such as propane, butane, isobutene, dimethyl ether;
styrene/PVP or styrene acrylamide copolymers;
insect repellants such as butylacetylaminopropionate.

Preferred preservatives include
benzyl alcohol;
zingerone.

In a preferred embodiment of the present invention, the sunscreen or daily care composition as defined by the above embodiments comprises at least one emollient.

Preferred emollients include
esters of linear or branched fatty acids with linear or branched fatty alcohols such as propylheptyl caprylate, coco caprylate, isopropyl myristate, ethylhexyl palmitate;

esters of aromatic carboxylic acids with linear or branched fatty alcohols such as $C_{12}$-$C_{15}$-alkyl benzoate, ethylhexyl benzoate, phenethyl benzoate;

di- and tricarboxylic acid esters with linear or branched alcohols such as dibutyl adipate, dicaprylyl carbonate, diisopropyl sebacate, triethyl citrate, tributyl citrate;

esters of hydroxycarboxylic acids with linear or branched fatty alcohols;

esters of linear or branched fatty acids with polyhydric alcohol such as butylene glycol dicaprylate/dicaprate;

mono-, di-, tri-glycerides based on $C_6$-$C_{18}$ fatty acids such as caprylic/capric triglycerides, coco glycerides;

Guerbet alcohols such as octyldodecynol;

hydrocarbons such as hydrogenated polyisobutene, mineral oil, squalene, isohexadecane;

ethers such as dicaprylyl ether;

silicone derivatives (organomodified polysiloxanes) such as dimethylpolysiloxane, cyclic silicones.

In another preferred embodiment of the present invention, the sunscreen or daily care composition as defined in the above embodiments comprises at least one perfume.

Preferred perfumes are selected from the group consisting of limonene, citral, linalool, alpha-isomethylionon, geraniol, citronellol, 2-isobutyl-4-hydroxy-4-methyltetrahydropyrane, 2-tert.-pentylcyclohexylacetate, 3-methyl-5-phenyl-1-pentanol, 7-acetyl-1,1,3,4,4,6-hexamethyltetraline, adipine acid diester, alpha-amylcinnamaldehyde, alpha-methylionon, amyl C butylphenylmethylpropionalcinnamal, amylsalicylate, amylcinnamylalcohol, anisalcohol, benzoin, benzylalcohol, benzylbenzoate, benzylcinnamate, benzylsalicylate, bergamot oil, bitter orange oil, butylphenylmethylpropioal, cardamom oil, cedrol, cinnamal, cinnamylalcohol, citronnellylmethylcrotonate, lemon oil, coumarin, diethylsuccinate, ethyllinalool, eugenol, *evernia furfuracea* extracte, *evernia prunastri* extracte, farensol, guajak wood oil, hexylcinnamal, hexylsalicylate, hydroxycitronellal, lavender oil, lemon oil, linaylacetate, mandarine oil, menthyl PCA, methylheptenone, nutmeg oil, rosemary oil, sweet orange oil, terpineol, tonka bean oil, triethylcitrate, vanillin and combinations thereof.

In connection with the above preferred embodiments, it is to be understood that if the sunscreen or daily care composition comprises two or more additives, combinations of the additives as defined above are also part of the invention.

In connection with the above preferred and particularly preferred embodiments, it is to be understood that the sunscreen or daily care composition, in its final formulation, may exist in a wide variety of presentation forms, which include liquid preparations as a W/O, O/W, O/W/O, W/O/W or PIT emulsion and all kinds of micro emulsions;

gels;

oil, cream, milk or lotion;

powder, a lacquer, a tablet or make-up;

sticks;

sprays (spray with propellant gas or pump-action spray) or an aerosol;

foams;

pastes.

In connection with the present invention, the following preferences regarding the use of the sunscreen or daily care composition according to the embodiments as listed above are relevant.

As indicated above, the present invention relates in one embodiment to the use of a sunscreen or daily care composition as defined above to enhance the photostability of the at least one UV filter selected from triazine derivatives.

In this connection it is to be understood that enhancing the photostability of the at least one UV filter selected from triazine derivatives means that the at least one UV filter selected from triazine derivatives is stabilized by the photostabilizer compounds in a way that a degradation of the UV filter selected from triazine derivatives upon UV radiation is prevented. An enhancement of the photostability of the at least one UV filter selected from triazine derivatives can be measured by the recovery of the at least one UV filter selected from triazine derivatives after certain irradiation duration times via HPLC measurement.

A skilled person is aware, that BMDBM is a frequently used UV absorber, which tends to isomerize under radiation to build a diketone in the triplet state. This diketone is very likely to undergo photolysis leading to a degradation of BMDBM. Furthermore, it has been found that the presence of BMDBM destabilizes the UV filter selected from triazine derivatives, i.e. ethylhexyl triazone, diethylhexyl butamido triazone, trisbiphenyl triazine and bis-ethylhexyloxyphenol methoxyphenyl triazine. Therefore, stabilizing agents need to be added to compositions comprising BMDBM, for example photo stable UV absorber such as octocrylene are commonly used. Thus, it has been a surprising finding by the inventors of the present invention, that in a composition according to the present invention, comprising BMDBM and UV filter selected from triazine, the triazine derivatives can be stabilized by photostabilizer according to the present invention in an octocrylene free sunscreen composition. In other words, this means that the presence of a photostabilizer according to the present invention, enhances the photostability of the UV filters present in the sunscreen or daily care composition according to the present invention, i.e. BMDBM and the destabilized triazine derivatives.

The present invention is further illustrated by the following examples.

EXAMPLES

Process of Manufacture of Sunscreen Compositions

The ingredients of part A, as well as the ingredients of part B as provided below in Tables 1.1, 1.2, 1.3 and 1.4 for each tested sunscreen composition were combined and heated to 80° C. respectively, wherein part A was added to part B under stirring and was further homogenized. Subsequently, the sunscreen composition was cooled down to room temperature under stirring and the pH of each composition was adjusted to 6.5-7.00 with NaOH (30%).

All amounts referred to in the following tables refer to the respective amounts in % by weight, based on the total weight of the composition.

Sunscreen Compositions

TABLE 1.1

Recovery of EHT

| Ingredient (Trade Name) | Comparative Comp. 1a | Comparative Comp. 1b | Comp. 2a | Comp. 2b | Comp. 2c | Comp. 2d | Comp. 2e | Comp. 2f | Comp. 2g | Comp. 2h | Comp. 2i |
|---|---|---|---|---|---|---|---|---|---|---|---|
| Part A | | | | | | | | | | | |
| Dibutyl adipate (Cetiol B) | 15.00 | 15.00 | 15.00 | 15.00 | 15.00 | 15.00 | 15.00 | 15.00 | 15.00 | 15.00 | 15.00 |
| $C_{12}$-$C_{15}$ alkyl benzoate (Cetiol AB) | 10.00 | 10.00 | 10.00 | 10.00 | 10.00 | 10.00 | 10.00 | 10.00 | 10.00 | 10.00 | 10.00 |
| Stearyl alcohol (Lanette 18) | 2.50 | 2.50 | 2.50 | 2.50 | 2.50 | 2.50 | 2.50 | 2.50 | 2.50 | 2.50 | 2.50 |
| Polyester-8 (Polycrylene) | — | — | 3.00 | — | — | — | — | — | — | — | — |
| Diethylhexyl 2,6-naphthalate (Corapan TQ) | — | — | — | 3.00 | — | — | — | — | — | — | — |
| Ethylhexyl methoxycrylene (SolaStay S1) | — | — | — | — | 3.00 | — | — | — | — | — | — |
| Trimethoxybenzylidene pentanedione (Synoxyl HSS) | — | — | — | — | — | 2.00 | — | — | — | — | — |
| Polyester-25 (Bis-Methoxycrylene/octyldodecyl adipic acid/methylpropane-diol copolymer) | — | — | — | — | — | — | 3.00 | — | — | — | — |
| Micah (=fused ring cyanoacrylate derivative) | — | — | — | — | — | — | — | 3.00 | — | — | — |
| Butyloctyl Salicylate | — | — | — | — | — | — | — | — | 3.00 | — | — |
| Benzotriazolyl Dodecyl p Cresol | — | — | — | — | — | — | — | — | — | 1.00 | — |
| Diethylhexyl Syringylidenemalonate | — | — | — | — | — | — | — | — | — | — | 1.00 |
| BMDBM | — | 2.00 | 2.00 | 2.00 | 2.00 | 2.00 | 2.00 | 2.00 | 2.00 | 2.00 | 2.00 |
| EHT (Uvinul T150) | 1.00 | 1.00 | 1.00 | 1.00 | 1.00 | 1.00 | 1.00 | 1.00 | 1.00 | 1.00 | 1.00 |
| BEMT (Tinosorb S) | — | — | — | — | — | — | — | — | — | — | — |
| Part B | | | | | | | | | | | |
| Water | qsp 100% | qsp 100% | qsp 100% | qsp 100% | qsp 100% | qsp 100% | qsp 100% | qsp 100% | qsp 100% | qsp 100% | qsp 100% |
| Glycerin | 2.00 | 2.00 | 2.00 | 2.00 | 2.00 | 2.00 | 2.00 | 2.00 | 2.00 | 2.00 | 2.00 |
| Disodium EDTA (EDTA BD) | 0.20 | 0.20 | 0.20 | 0.20 | 0.20 | 0.20 | 0.20 | 0.20 | 0.20 | 0.20 | 0.20 |
| Acrylates/Beheneth-25 methacrylate copolymer (Tinovis GTC UP) | 2.00 | 2.00 | 2.00 | 2.00 | 2.00 | 2.00 | 2.00 | 2.00 | 2.00 | 2.00 | 2.00 |
| Xanthan Gum (Rheocare XGN) | 0.50 | 0.50 | 0.50 | 0.50 | 0.50 | 0.50 | 0.50 | 0.50 | 0.50 | 0.50 | 0.50 |

TABLE 1.2

Recovery of BEMT

| Ingredient (Trade Name) | Comparative Comp. 1c | Comparative Comp. 1d | Comp. 3a | Comp. 3b | Comp. 3c | Comp. 3d | Comp. 3e | Comp. 3f | Comp. 3g | Comp. 3h |
|---|---|---|---|---|---|---|---|---|---|---|
| Part A | | | | | | | | | | |
| Dibutyl adipate (Cetiol B) | 10.00 | 10.00 | 10.00 | 10.00 | 10.00 | 10.00 | 10.00 | 10.00 | 10.00 | 10.00 |
| $C_{12}$-$C_{15}$ alkyl benzoate (Cetiol AB) | 10.00 | 10.00 | 10.00 | 10.00 | 10.00 | 10.00 | 10.00 | 10.00 | 10.00 | 10.00 |
| Stearyl alcohol (Lanette 18) | 2.50 | 2.50 | 2.50 | 2.50 | 2.50 | 2.50 | 2.50 | 2.50 | 2.50 | 2.50 |
| Polyester-8 (Polycrylene) | — | — | 3.00 | — | — | — | — | — | — | — |
| Diethylhexyl 2,6-naphthalate (Corapan TQ) | — | — | — | 3.00 | — | — | — | — | — | — |
| Ethylhexyl methoxycrylene (SolaStay Si) | — | — | — | — | 3.00 | — | — | — | — | — |

TABLE 1.2-continued

Recovery of BEMT

| Ingredient (Trade Name) | Comparative Comp. 1c | Comparative Comp. 1d | Comp. 3a | Comp. 3b | Comp. 3c | Comp. 3d | Comp. 3e | Comp. 3f | Comp. 3g | Comp. 3h |
|---|---|---|---|---|---|---|---|---|---|---|
| Trimethoxybenzylidene pentanedione (Synoxyl HSS) | — | — | — | — | — | 3.00 | — | — | — | — |
| Polyester-25 (Bis-Methoxycrylene/ octyldodecyl adipic acid/methylpropane-diol copolymer) | — | — | — | — | — | — | — | — | 3.00 | — |
| Micah (=fused ring cyanoacrylate derivative) | — | — | — | — | — | — | — | 3.00 | — | — |
| Benzotriazolyl Dodecyl p Cresol | — | — | — | — | — | — | — | — | — | 1.00 |
| BMDBM | — | 3.00 | 3.00 | 3.00 | 3.00 | 3.00 | 3.00 | 3.00 | 3.00 | 3.00 |
| EHT (Uvinul T150) | — | — | — | — | — | — | — | — | — | — |
| BEMT (Tinosorb S) | 1.00 | 1.00 | 1.00 | 1.00 | 1.00 | 1.00 | 1.00 | 1.00 | 1.00 | 1.00 |
| Part B |  |  |  |  |  |  |  |  |  |  |
| Water | qsp 100% | qsp 100% | qsp 100% | qsp 100% | qsp 100% | qsp 100% | qsp 100% | qsp 100% | qsp 100% | qsp 100% |
| Glycerin | 2.00 | 2.00 | 2.00 | 2.00 | 2.00 | 2.00 | 2.00 | 2.00 | 2.00 | 2.00 |
| Disodium EDTA (EDTA BD) | 0.20 | 0.20 | 0.20 | 0.20 | 0.20 | 0.20 | 0.20 | 0.20 | 0.20 | 0.20 |
| Acrylates/Beheneth-25 methacrylate copolymer (Tinovis GTC UP) | 2.00 | 2.00 | 2.00 | 2.00 | 2.00 | 2.00 | 2.00 | 2.00 | 2.00 | 2.00 |
| Xanthan Gum (Rheocare XGN) | 0.50 | 0.50 | 0.50 | 0.50 | 0.50 | 0.50 | 0.50 | 0.50 | 0.50 | 0.50 |

TABLE 1.3

Recovery of DBT

| Ingredient (Trade Name) | Comparative Comp. 1e | Comparative Comp. 1f | Comp. 4a | Comp. 4b | Comp. 4c |
|---|---|---|---|---|---|
| Part A |  |  |  |  |  |
| Dibutyl adipate (Cetiol B) | 15.00 | 15.00 | 15.00 | 15.00 | 15.00 |
| $C_{12}$-$C_{15}$ alkyl benzoate (Cetiol AB) | 10.00 | 10.00 | 10.00 | 10.00 | 10.00 |
| Stearyl alcohol (Lanette 18) | 2.50 | 2.50 | 2.50 | 2.50 | 2.50 |
| Polyester-8 (Polycrylene) | — | — | 3.00 | — | — |
| Diethylhexyl 2,6-naphthalate (Corapan TQ) | — | — | — | 3.00 | — |
| Butyloctyl Salicylate | — | — | — | — | 3.00 |
| BMDBM | — | 2.00 | 2.00 | 2.00 | 2.00 |
| DBT (Uvasorb H EB) | 1.00 | 1.00 | 1.00 | 1.00 | 1.00 |
| Part B |  |  |  |  |  |
| Water | qsp 100% | qsp 100% | qsp 100% | qsp 100% | qsp 100% |
| Glycerin | 2.00 | 2.00 | 2.00 | 2.00 | 2.00 |
| Disodium EDTA (EDTA BD) | 0.20 | 0.20 | 0.20 | 0.20 | 0.20 |
| Acrylates/Beheneth-25 methacrylate copolymer (Tinovis GTC UP) | 2.00 | 2.00 | 2.00 | 2.00 | 2.00 |
| Xanthan Gum (Rheocare XGN) | 0.50 | 0.50 | 0.50 | 0.50 | 0.50 |

TABLE 1.4

Recovery of BEMT + EHT

| Ingredient (Trade Name) | Comparative Comp. 1g | Comparative Comp. 1h | Comp. 5a | Comp. 5b | Comp. 5c | Comp. 5d |
|---|---|---|---|---|---|---|
| Part A | | | | | | |
| Dibutyl adipate (Cetiol B) | 15.00 | 15.00 | 15.00 | 15.00 | 15.00 | 15.00 |
| $C_{12}$-$C_{15}$ alkyl benzoate (Cetiol AB) | 10.00 | 10.00 | 10.00 | 10.00 | 10.00 | 10.00 |
| Stearyl alcohol (Lanette 18) | 2.50 | 2.50 | 2.50 | 2.50 | 2.50 | 2.50 |
| Polyester-8 (Polycrylene) | — | — | — | — | — | — |
| Diethylhexyl 2,6-naphthalate (Corapan TQ) | — | — | — | — | 3.00 | |
| Ethylhexyl methoxycrylene (SolaStay Si) | | | 3.00 | | | |
| Trimethoxybenzylidene pentanedione (Synoxyl HSS) | — | — | — | 3.00 | | |
| Butyloctyl Salicylate | | | | | 3.00 | |
| BMDBM | — | 3.00 | 3.00 | 3.00 | 3.00 | 3.00 |
| EHT (Uvinul T150) | 1.00 | 1.00 | 1.00 | 1.00 | 1.00 | 1.00 |
| BEMT (Tinosorb S) | 1.00 | 1.00 | 1.00 | 1.00 | 1.00 | 1.00 |
| Part B | | | | | | |
| Water | qsp 100% | qsp 100% | qsp 100% | qsp 100% | qsp 100% | qsp 100% |
| Glycerin | 2.00 | 2.00 | 2.00 | 2.00 | 2.00 | 2.00 |
| Disodium EDTA (EDTA BD) | 0.20 | 0.20 | 0.20 | 0.20 | 0.20 | 0.20 |
| Acrylates/Beheneth-25 methacrylate copolymer (Tinovis GTC UP) | 2.00 | 2.00 | 2.00 | 2.00 | 2.00 | 2.00 |
| Xanthan Gum (Rheocare XGN) | 0.50 | 0.50 | 0.50 | 0.50 | 0.50 | 0.50 |

Recovery Measurements on Photo Stability of EHT

The UV filter compositions as defined in Tables 1.1 to 1.4 are applied on roughened quartz plates (2 ml/cm$^2$). Plates are irradiated using Atlas CPS device at different duration times (MED=Minimal Erythema Dose):
- 0 h (0 MED, no irradiation)
- 1 h (5 MED),
- 2 h (10 MED),
- 4 h (20 MED).

In total, four plates are prepared for each irradiation condition. After irradiation, each plate is rinsed off with tetrahydrofuran. The rinsing solution is further analyzed via HPLC to determine the recovery of EHT.

Recovery Measurements on Photo Stability of BEMT

The UV filter compositions as defined in Table 1.2 are applied on roughened quartz plates (2 ml/cm$^2$). Plates are irradiated using Atlas CPS device at different duration times (MED=Minimal Erythema Dose):
- 0 h (0 MED, no irradiation)
- 1 h (5 MED),
- 2 h (10 MED),
- 4 h (20 MED).

In total, four plates are prepared for each irradiation condition. After irradiation, each plate is rinsed off with tetrahydrofuran. The rinsing solution is further analyzed via HPLC to determine the recovery of BEMT.

TABLE 2.1

| | Comparative Comp. 1a | Comparative Comp. 1b | Comp. 2a | Comp. 2b | Comp. 2c |
|---|---|---|---|---|---|
| 0 MED | 100% | 100% | 100% | 100% | 100% |
| 5 MED | 97% | 92% | 97% | 94% | 102% |
| 10 MED | 94% | 79% | 100% | 87% | 101% |
| 20 MED | 90% | 31% | 88% | 79% | 100% |

| | Comp. 2d | Comp. 2e | Comp. 2f | Comp. 2g | Comp. 2h | Comp. 2i |
|---|---|---|---|---|---|---|
| 0 MED | 100% | 100% | 100% | 100% | 100% | 100% |
| 5 MED | 99% | 106% | 102% | 92% | 101% | 99% |
| 10 MED | 102% | 100% | 102% | 87% | 96% | 85% |
| 20 MED | 96% | 96% | 98% | 68% | 85% | 49% |

A person skilled in the art is aware that data above 100% after irradiation are due to common measurement fluctuations.

TABLE 2.2

|  | Comparative Comp. 1c | Comparative Comp. 1d | Comp. 3a | Comp. 3b | Comp. 3c |
|---|---|---|---|---|---|
| 0 MED | 100% | 100% | 100% | 100% | 100% |
| 5 MED | 96% | 93% | 104% | 94% | 106% |
| 10 MED | 99% | 84% | 99% | 93% | 104% |
| 20 MED | 98% | 78% | 96% | 86% | 100% |

|  | Comp. 3d | Comp. 3e | Comp. 3f | Comp. 3g | Comp. 3h |
|---|---|---|---|---|---|
| 0 MED | 100% | 100% | 100% | 100% | 100% |
| 5 MED | 94% | 96% | 98% | 102% | 102% |
| 10 MED | 94% | 92% | 99% | 98% | 98% |
| 20 MED | 92% | 86% | 95% | 90% | 90% |

A person skilled in the art is aware that data above 100% after irradiation are due to common measurement fluctuations.

Recovery Measurements on Photo Stability of DBT

The UV filter compositions as defined in Table 1.3 are applied on roughened quartz plates (2 ml/cm$^2$). Plates are irradiated using Atlas CPS device at different duration times (MED=Minimal Erythema Dose):

0 h (0 MED, no irradiation)
1 h (5 MED),
2 h (10 MED),
4 h (20 MED).

In total, four plates are prepared for each irradiation condition. After irradiation, each plate is rinsed off with tetrahydrofuran. The rinsing solution is further analyzed via HPLC to determine the recovery of DBT.

TABLE 2.3

|  | Comparative Comp. 1e | Comparative Comp. 1f | Comp. 4a | Comp. 4b | Comp. 4c |
|---|---|---|---|---|---|
| 0 MED | 100% | 100% | 100% | 100% | 100% |
| 5 MED | 92% | 85% | 101% | 95% | 91% |
| 10 MED | 84% | 60% | 101% | 82% | 83% |
| 20 MED | 62% | 30% | 85% | 68% | 71% |

A person skilled in the art is aware that data above 100% after irradiation are due to common measurement fluctuations.

Recovery Measurements on Photo Stability of BEMT+EHT

The UV filter compositions as defined in Table 1.4 are applied on roughened quartz plates (2 ml/cm$^2$). Plates are irradiated using Atlas CPS device at different duration times (MED=Minimal Erythema Dose):

0 h (0 MED, no irradiation)
1 h (5 MED),
2 h (10 MED),
4 h (20 MED),
10 h (50 MED).

In total, four plates are prepared for each irradiation condition. After irradiation, each plate is rinsed off with tetrahydrofuran. The rinsing solution is further analyzed via HPLC to determine the recovery of BEMT+EHT.

TABLE 2.4

|  | Comparative Comp. 1g | | Comparative Comp. 1h | | Comp. 5a | |
|---|---|---|---|---|---|---|
|  | BEMT | EHT | BEMT | EHT | BEMT | EHT |
| 0 MED | 100% | 100% | 100% | 100% | 100% | 100% |
| 5 MED | 102% | 103% | 93% | 95% | 97% | 97% |
| 10 MED | 99% | 99% | 87% | 89% | 99% | 99% |
| 20 MED | 100% | 100% | 74% | 76% | 97% | 98% |
| 50 MED | 99% | 99% | 53% | 47% | 92% | 95% |

|  | Comp. 5b | | Comp. 5c | | Comp. 5d | |
|---|---|---|---|---|---|---|
|  | BEMT | EHT | BEMT | EHT | BEMT | EHT |
| 0 MED | 100% | 100% | 100% | 100% | 100% | 100% |
| 5 MED | 103% | 103% | 97% | 98% | 97% | 98% |
| 10 MED | 104% | 103% | 89% | 94% | 95% | 98% |
| 20 MED | 101% | 100% | 85% | 90% | 90% | 95% |
| 50 MED | 95% | 89% | 69% | 68% | 70% | 73% |

A person skilled in the art is aware that data above 100% after irradiation are due to common measurement fluctuations.

The invention claimed is:

1. A sunscreen or daily care composition comprising
   (i) 1-(4-(1,1-dimethylethyl)phenyl)-3-(4-methoxyphenyl) propane-1,3-dione (INCI butyl methoxydibenzoylmethane); and
   (ii) at least one UV filter which is a triazine derivative selected from the group consisting of 4,4',4"-(1,3,5-triazine-2,4,6-triyltriimino)tris-benzoic acid-tris(2-ethylhexyl)ester (INCI ethylhexyl triazone), 4,4'-[[6-[[4-[[(1,1-dimethylethyl)amino]carbonyl]phenyl]amino]-1,3,5-triazin-2,4-diyl]diimino]bis-benzoic acid-bis(2-ethylhexyl)ester (INCI diethylhexyl-butamidotriazone), 2,4-bis-{[4-(2-ethyl-hexyloxy)-2-hydroxy]-phenyl}-6-(4-methoxyphenyl)-1,3,5 triazine (INCI bis-ethylhexyloxyphenol methoxyphenyl triazine) and combinations thereof; and
   (iii) at least one photostabilizer selected from the group consisting of butyloctyl salicylate, benzotriazolyl dodecyl p cresol, ethylhexyl methoxycrylene, polyester-8, diethylhexyl syringylidenemalonate, trimethoxybenzylidene pentanedione, diethylhexyl 2,6-naphthalate, a fused ring cyanoacrylate derivative, polyester-25 and combinations thereof;
   wherein the composition does not comprise ethylhexyl-2-cyano-3,3-diphenyl-acrylate (INCI octocrylene) and 2-ethylhexyl-(2E)-3-(4-methoxyphenyl) acrylate (INCI ethylhexyl methoxy cinnamate).

2. The sunscreen or daily care composition according to claim 1, wherein the composition is free of any cinnamic acid derivatives.

3. The sunscreen or daily care composition according to claim 1, wherein the composition comprises 1-(4-(1,1-dimethylethyl)phenyl)-3-(4-methoxyphenyl) propane-1,3-dione (INCI butyl methoxydibenzoylmethane) in an amount of from 1% to 5% by weight, based on the total weight of the composition.

4. The sunscreen or daily care composition according to claim 1, wherein the composition comprises the at least one UV filter in an amount of from 0.5% to 10% by weight, based on the total weight of the composition.

5. The sunscreen or daily care composition according to claim 1, wherein the composition comprises the at least one photostabilizer in an amount of from 0.5% to 5% by weight, based on the total weight of the composition.

6. The sunscreen or daily care composition according to claim 1, wherein the composition is free of parabens.

7. The sunscreen or daily care composition according to claim 1, wherein the composition comprises at least one perfume.

8. The sunscreen or daily care composition according to claim 1, wherein the composition comprises at least one emollient.

9. The sunscreen or daily care composition according to claim 1, wherein the composition comprises the at least one UV filter in an amount of from 0.5% to 5% by weight based on the total weight of the composition.

* * * * *